United States Patent
Cooks et al.

(10) Patent No.: US 9,921,233 B2
(45) Date of Patent: *Mar. 20, 2018

(54) COMBINED DESI AND OPTICAL IMAGING ANALYSIS OF TISSUES

(71) Applicant: Purdue Research Foundation, West Lafayette, IN (US)

(72) Inventors: Robert Graham Cooks, West Lafayette, IN (US); Livia Schiavinato Eberlin, Lafayette, IN (US); Christina Ramires Ferreira, West Lafayette, IN (US); Allison Lisa Dill, Indianapolis, IN (US); Demian R. Ifa, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 172 days.

This patent is subject to a terminal disclaimer.

(21) Appl. No.: 14/880,623

(22) Filed: Oct. 12, 2015

(65) Prior Publication Data

US 2016/0047831 A1    Feb. 18, 2016

Related U.S. Application Data

(63) Continuation of application No. 13/475,305, filed on May 18, 2012, now Pat. No. 9,157,921.
(Continued)

(51) Int. Cl.
*G01N 24/00*    (2006.01)
*G01N 33/92*    (2006.01)
(Continued)

(52) U.S. Cl.
CPC .......... *G01N 33/92* (2013.01); *H01J 49/0036* (2013.01); *H01J 49/165* (2013.01); *H01J 49/0004* (2013.01); *H01J 49/142* (2013.01)

(58) Field of Classification Search
CPC .. H01J 49/0004; H01J 49/164; H01J 49/0418; H01J 49/40; H01J 49/04; H01J 49/0027; H01J 49/165; H01J 49/0463; H01J 49/142; H01J 49/16; H01J 49/0059; H01J 49/161; H01J 49/00; H01J 49/004
See application file for complete search history.

(56) References Cited

U.S. PATENT DOCUMENTS

| 7,335,897 B2 | 2/2008 | Takats et al. |
| 2012/0119079 A1 | 5/2012 | Ouyang et al. |

FOREIGN PATENT DOCUMENTS

| WO | 2009/102766 A1 | 8/2009 |
| WO | 2010/127059 A1 | 11/2010 |

OTHER PUBLICATIONS

Wiseman et al., "Tissue Imaging at Atmospheric Pressure Using Desorption Electrospray Ionization (DESI) Mass Spectrometry" Angew. Chem. Int. Ed., 2006, v. 45, pp. 7188-7192.*
(Continued)

*Primary Examiner* — Yelena G Gakh
(74) *Attorney, Agent, or Firm* — Brown Rudnick LLP; Adam M. Schoen

(57) ABSTRACT

The invention generally relates to mass spectral analysis. In certain embodiments, methods of the invention involve analyzing a lipid containing sample using a mass spectrometry technique, in which the technique utilizes a liquid phase that does not destroy native tissue morphology during analysis.

19 Claims, 8 Drawing Sheets

Related U.S. Application Data

(60) Provisional application No. 61/487,363, filed on May 18, 2011.

(51) Int. Cl.
*H01J 49/16* (2006.01)
*H01J 49/00* (2006.01)
*H01J 49/14* (2006.01)

(56) References Cited

OTHER PUBLICATIONS

Abe, et al., "Inkjet-Printed Microfluidic Multianalyte Chemical Sensing Paper," Anal. Chemistry, 2008, 80, 6928-6934.
Agar, et al., "Development of stereotactic mass spectrometry for brain tumor surgery," Neurosurgery 68, 2011, 280-289, Discussion 290.
Amary, et al., "IDH1 and IDH2 mutations are frequent events in central chondrosarcoma and central and periosteal chondromas but not in other mesenchymal tumours," J Pathol, 2011, 224, 334-343.
Andronesi, et al., "Detection of 2-hydroxyglutarate in IDH-mutated glioma patients by in vivo spectral-editing and 2D correlation magnetic resonance spectroscopy," Sci Transl Med 4, 2012, 116ra114.
Borger, et al., "Frequent mutation of isocitrate dehydrogenase (IDH)1 and IDH2 in cholangiocarcinoma identified through broad-based tumor genotyping," Oncologist, 2012, 17, 72-79.
Bruzewicz, et al., "Low-Cost Printing of Poly(dimethylsiloxane) Barriers to Define Microchannels in Paper," Anal. Chemistry, 2008, 80, 3387-3392.
Capper, et al., Characterization of R132H mutation-specific IDH1 antibody binding in brain tumors, Brain Pathol, 2010, 20, 245-254.
Carroll, et al., "Atmospheric Pressure Ionization Mass Spectrometry: Corona Discharge Ion Source for Use in Liquid Chromatograph-Mass Spectrometer-Computer Analytical System," Anal. Chemistry, 1975, 47, 2369-2373.
Chi, et al., "Prospective, high-throughput molecular profiling of human gliomas," J Neurooncol, 2012, 110, 89-98.
Choi, et al., 2-hydroxyglutarate detection by magnetic resonance spectroscopy in IDH-mutated patients with gliomas, Nat Med, 2012, 18, 624-629.
Cody, et al., Versatile New Ion Source for the Analysis of Materials in Open Air under Ambient Condition, Anal. Chemistry, 2005, 77, 2297-2302.
Cooks, et al., "New ionization methods and miniature mass spectrometers for biomedicine: DESI imaging for cancer diagnostics and paper spray ionization for therapeutic drug monitoring," Faraday Discussions, 2011, 149, 247-267.
Dang, et al., "Cancer-associated IDH1 mutations produce 2-hydroxyglutarate," Nature, 2009, 462, 739-744.
Dias-Santagata, et al., "BRAF V600E mutations are common in pleomorphic xanthoastrocytoma: diagnostic and therapeutic implications," PLoS One 6, 2011, e17948.
Dias-Santagata, et al., "Rapid targeted mutational analysis of human tumours: a clinical platform to guide personalized cancer medicine," EMBO Mol Med, 2010, 2, 146-158.
Dill, et al., Lipid profiles of canine invasive transitional cell carcinoma of the urinary bladder and adjacent normal tissue by desorption electrospray ionization imaging mass spectrometry, Anal Chemistry, 2009, 81, 8758-8764.
Dill, et al., "Multivariate statistical differentiation of renal cell carcinomas based on lipidomic analysis by ambient ionization imaging mass spectrometry," Analytical and Bioanalytical Chemistry, 2010, 398, 2969-2978.
Dill, et al., "Multivariate Statistical Identification of Human Bladder Carcinomas Using Ambient Ionization Imaging Mass Spectrometry," A European Journal, 2011, 17, 2897-2902.
Eberlin, et al., "Cholesterol Sulfate Imaging in Human Prostate Cancer Tissue by Desorption Electrospray Ionization Mass Spectrometry," Analytical Chemistry, 2010, 82, 3430-3434.
Eberlin, et al., "Ambient mass spectrometry for the intraoperative molecular diagnosis of human brain tumors," Proc Natl Acad Sci USA, 2013, 110(5), 1611-1616.
Eberlin, et al., Classifying human brain tumors by lipid imaging with mass spectrometry, Cancer Research, 2012, 72, 645-654.
Eberlin, et al., "Discrimination of human astrocytoma subtypes by lipid analysis using desorption electrospray ionization imaging mass spectrometry," Angew Chemistry Int, 2010, Ed Engl 49, 5953-5956.
Eberlin, et al., "Nondestructive, histologically compatible tissue imaging by desorption electrospray ionization mass spectrometry," ChemBioChem, 2011, 12, 2129-2132.
Elhawary, et al. "Intraoperative real-time querying of white matter tracts during frameless stereotactic neuronavigation," Neurosurgery, 2011, 68, 506-516, Discussion 516.
Elkhaled, et al., "Magnetic resonance of 2-hydroxyglutarate in IDH1-mutated low-grade gliomas," Science Translational Medicine, 2012, 4, 116ra115.
Ellis, et al. "Imaging of Human Lens Lipids by Desorption Electrospray Ionization Mass Spectrometry," J. Am. Soc. Mass Spectrom, 2010, 21(12), 2095-2104.
Fenn, et al. Electrospray Ionization for Mass Spectrometry of Large Biomolecules, Science, 1989, 246, 64-71.
Guo, et al., "The relationship between Cho/NAA and glioma metabolism: implementation for margin delineation of cerebral gliomas," Acta Neurochir (Wien), 2012, 154, 1361-1370; Discussion 1370.
Harris, et al., "Ambient sampling/ionization mass spectrometry: applications and current trends," Analytical Chemistry, 2011, 83, 4508-4538.
Hartmann, et al., "Type and frequency of IDH1 and IDH2 mutations are related to astrocytic and oligodendroglial differentiation and age: a study of 1,010 diffuse gliomas," Acta Neuropathol, 2009, 118, 469-474.
Ifa, et al., "Desorption electrospray ionization and other ambient ionization methods: current progress and preview," Analyst, 2010, 135, 669-681.
Ifa, et al., "Latent Fingerprint Chemical Imaging by Mass Spectrometry," Int. J. Mass Spectrom, 2007, 259(8), 805.
Jolesz, et al, "Intraoperative imaging in neurosurgery: Where will the future take us?" Acta Neurochir Suppl, 2011, 109, 21-25.
Kalinina, et al., "Detection of "oncometabolite" 2-hydroxyglutarate by magnetic resonance analysis as a biomarker of IDH1/2 mutations in glioma," J Mol Med (Berl), 2012, 90, 1161-1171.
Kogelschatz, "Dielectric-barrier Discharges: Their History, Discharge Physics, and Industrial Applications," Plasma Chemistry and Plasma Processing, 2003, 23, 1-46.
Koivunen, et al., "Transformation by the (R)-enantiomer of 2-hydroxyglutarate linked to EGLN activation," Nature, 2012, 483, 484-488.
Lai, et al, "Evidence for sequenced molecular evolution of IDH1 mutant glioblastoma from a distinct cell of origin," J Clin Oncol, 2011, 29, 4482-4490.
Laiko, et al., "Atmospheric Pressure Matrix-Assisted Laser Desoprtion/Ionization Mass Spectrometry," Analytical Chemistry, 2000, 72, 652-657.
Lazovic, et al., "Detection of 2-hydroxyglutaric acid in vivo by proton magnetic resonance spectroscopy in U87 glioma cells overexpressing isocitrate dehydrogenase-1 mutation," Neuro Oncol, 2012, 14, 1465-1472.
Li, et al., "Paper-Based Microfluidic Devices by Plasma Treatment," Anal. Chemistry, 2008, 80, 9131-9134.
Linehan, et al., "The genetic basis of kidney cancer: a metabolic disease," Nat Rev Urol, 2010, 7, 277-285.
Losman, et al., "(R)-2-Hydroxyglutarate is Sufficient to Promote Leukemogenesis and its Effects Are Reversible," Science, 2013, 339, 1621-1624.
Lu, et al., "IDH mutation impairs histone demethylation and results in a block to cell differentiation," Nature, 2012, 483, 474-478.
Manicke, et al., "Imaging of Lipids in Atheroma by Desorption Electrospray Ionization Mass Spectrometry," Analytical Chemistry, 2009, 81(21), 8702-8707.

(56) References Cited

OTHER PUBLICATIONS

Mardis, et al., "Recurring mutations found by sequencing an acute myeloid leukemia genome," N Engl J Med, 2009, 361, 1058-1066.
Martinez, et al., "Flash: A rapid method for prototyping paper-based microfluidic devices," Lab Chip 2008, 8, 2146-2150.
Martinez, et al., "Patterned Paper as a Platform for Inexpensive, Low-Volume, Portable Bioassays," Angew Chem Int, Ed., 2007, 46, 1318-1320.
Martinez, et al., "Three-dimensional microfluidic devices fabricated in layered paper and tape," Proc. Natl Acad. Sci. USA, 2008, 105, 19606-19611.
Nemes, "Ambient mass spectrometry for in vivo local analysis and in situ molecular tissue imaging," Trends in Analytical Chemistry, 2012, 34, 22-33.
Parsons, et al., "An integrated genomic analysis of human glioblastoma multiforme," Science, 2008, 321, 1807-1812.
Pope, et al., "Non-invasive detection of 2-hydroxyglutarate and other metabolites in IDH1 mutant glioma patients using magnetic resonance spectroscopy," J Neurooncol, 2012, 107, 197-205.
Rohle, et al., "An Inhibitor of Mutant IDH1 Delays Growth and Promotes Differentiation of Glioma Cells," Science, 2013, 340, 626-630.
Schwamborn, et al., "Identifying prostate carcinoma by MALDI-Imaging," International Journal of Molecular Medicine, 2007, 20(2), 155-159.
Shiea, et al., "Electrospray-assisted laser desorption/ionization mass spectrometry for direct ambient analysis of solids," J. Rapid Communications in Mass Spectrometry, 2005, 19, 3701-3704.
Takats, et al., "Mass spectrometry sampling under ambient conditions with desorption electrospray ionization," Science, 2004, 306, 471-473.
Tanaka, et al., "Protein and Plymer Analyses up to m/z 100 000 by Laser Ionization Time-of-Flight Mass Spectrometry," Rapid Comm Mass Spectrom, 1988, 2, 151-153,1988.
Turcan, et al., "IDH1 mutation is sufficient to establish the glioma hypermethylator phenotype," Nature, 2012, 483, 479-483.
Van Berkel, et al., "Established and emerging atmospheric pressure surface sampling/ionization techniques for mass spectrometry," J Mass Spectrom, 2008, 43, 1161-1180.
Wang, et al., "Targeted Inhibition of Mutant IDH2 in Leukemia Cells Induces Cellular Differentiation," Science, 2013, 340, 622-625.
Weller, et al., "Isocitrate dehydrogenase mutations: a challenge to traditional views on the genesis and malignant progression of gliomas," Glia, 2011, 59, 1200-1204.
Wiseman, et al., "Ambient molecular imaging by desorption electrospray ionization mass spectrometry," Nat Protoc 3, 2008, 517-524.
Wiseman, et al., "Desorption electrospray ionization mass spectrometry: Imaging drugs and metabolites in tissues," Proc Natl Acad Sci USA, 2008, 105, 18120-18125.
Xu, et al., "Oncometabolite 2-hydroxyglutarate is a competitive inhibitor of alpha-ketoglutarate-dependent dioxygenases," Cancer Cell, 2011, 19, 17-30.
Yamashita, et al., "Electrospray Ion Source. Another Variation on the Free-Jet Theme," J. Phys Chem, 1984, 88, 4451-4459.
Yan, et al., "IDH1 and IDH2 mutations in gliomas," N Engl J Med, 2009, 360, 765-773.
Aston Labs report "Histologically compatible tissue imaging", published May 6, 2009.

\* cited by examiner

PS 18:0 / 22:6

ST (24:1)

ST (24:0)

PI 18:0/20:4

FA (20:4)

H&E stained

FIG. 4I        Overlaid

Ion image (*m/z* 537.2) + H&E stained

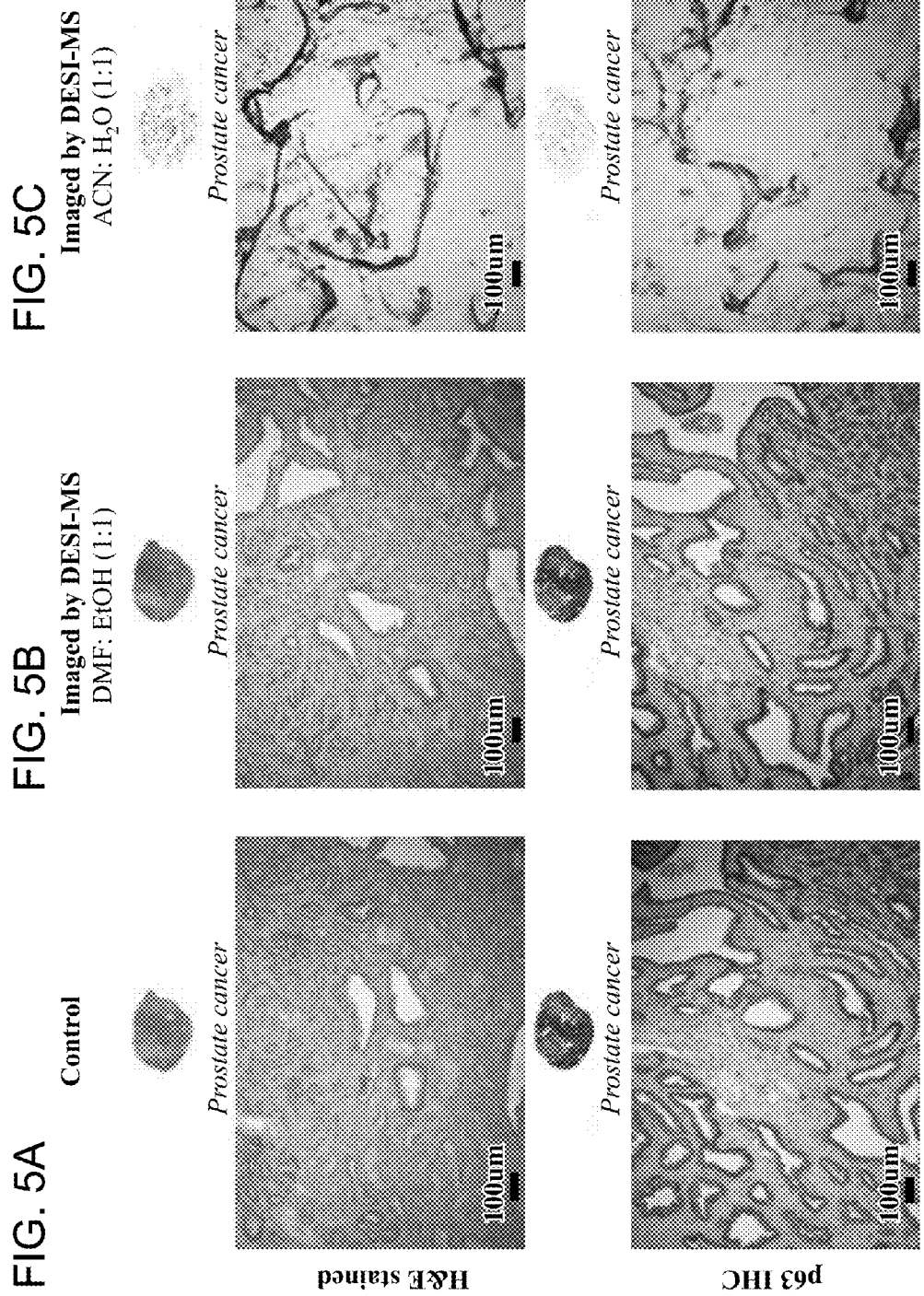

COMBINED DESI AND OPTICAL IMAGING ANALYSIS OF TISSUES

RELATED APPLICATION

The present application is a continuation of U.S. nonprovisional application Ser. No. 13/475,305, filed May 18, 2012, which claims the benefit of and priority to U.S. provisional patent application Ser. No. 61/487,363, filed May 18, 2011, the content of each of which is incorporated by reference herein in its entirety.

GOVERNMENT INTEREST

This invention was made with government support under EB009459 awarded by National Institutes of Health. The government has certain rights in the invention.

FIELD OF THE INVENTION

The invention generally relates to mass spectral analysis.

BACKGROUND

Imaging mass spectrometry (MS) is currently in its translational phase as a tool in medical histopathology. Many biological applications are being pursued due to its capability to provide comprehensive information on the distribution of multiple endogenous and exogenous molecules within animal tissues (van Hove E R A, Smith D F, & Heeren R M A (2010), J. Chromatogr. A 1217(25):3946-3954; Watrous J D, Alexandrov T, & Dorrestein P C (2011), Journal of Mass Spectrometry 46(2):209-222). Imaging MS has the capability of mapping drugs, metabolites, lipids, peptides and proteins in thin tissue sections with high specificity and without the need of fluorescent or radioactive labeling normally used in histochemical protocols (Schwamborn K & Caprioli R M (2010), Mol. Oncol. 4(6):529-538; and Chughtai K & Heeren R M A (2010), Chem. Rev. 110(5): 3237-3277).

Within the imaging MS techniques (Alberici R M, et al. (2010), Analytical and Bioanalytical Chemistry 398(1):265-294), ambient ionization techniques such as desorption electrospray ionization mass spectrometry (DESI-MS) have been rapidly emerging and have the advantage of being performed at atmospheric pressure without the need for sample preparation (Ifa D R, Wu C P, Ouyang Z, & Cooks R G (2010), Analyst 135(4):669-681). Other imaging techniques such as matrix assisted laser desorption ionization (MALDI; Oppenheimer S R, Mi D M, Sanders M E, & Caprioli R M (2010), Journal of Proteome Research 9(5): 2182-2190) and secondary ion mass spectrometry (SIMS; Fletcher J S & Vickerman J C (2010), Analytical and Bioanalytical Chemistry 396(1):85-104) are commonly performed under high-vacuum conditions and the former requires careful sample preparation through the application of a matrix. More recently, much effort has been put towards advancing ambient imaging mass spectrometry within the biomedical field, especially in cancer diagnostics (Dill A L, Eberlin L S, Ifa D R, & Cooks R G (2011), Chemical Communications 47(10):2741-2746). The prospect of improving the accuracy of histopathological cancer evaluation by adding chemical information to the morphological microscopic analysis, especially related to cancer diagnosis and grading represents an attainable and relevant medical application. Nonetheless, technical challenges remain and validation studies are still needed to successfully merge microscopic and mass spectrometric information into routine histopathology workflow.

As the ability of DESI-MS as a diagnostic tool is demonstrated in many studies, this capability must be validated through extensive chemical and microscopic examination of tissue sections and development of classification rules relating MS imaging molecular information to traditional pathology. The correlation between histology and DESI-MS has thus far been performed by comparing the ion images obtained to the diagnosis from pathological evaluation of a serial hematoxylin and eosin (H&E) stained section (Masterson T A, et al. (2010) Distinctive Glycerophospholipid Profiles of Human Seminoma and Adjacent Normal Tissues by Desorption Electrospray Ionization Imaging Mass Spectrometry. J. Am. Soc. Mass. Spectrom. in press). Even though this strategy is sufficient for optical image evaluation under routine microscopic pathology, workflow practicality and unambiguous correlation demand the use of the same tissue section for morphological and MS imaging evaluation.

The first strategy reported for conducting histopathology and imaging MS analysis on the same tissue section was the development of MALDI imaging compatible dyes, which provide limited histological details (Chaurand P, et al. (2004), Analytical Chemistry 76(4):1145-1155). Tissue section staining after MALDI imaging spectra acquisition and matrix removal is considered the most promising approach to pair MALDI imaging and histological staining, a strategy named post-acquisition staining (Crecelius A C, et al. (2005), Journal of the American Society for Mass Spectrometry 16(7):1093-1099). As an ambient imaging MS technique, DESI-MS frees the user from the need of a homogeneous matrix deposition on the sample.

A limitation preventing DESI-MS imaging compatibility with histochemistry is that the most common DESI solvent systems, methanol/water and acetonitrile/water 1:1 (v/v), completely destroy the native tissue morphology during analysis.

SUMMARY

The present invention provides new methodologies by which mass spectral analysis of tissue (such as ambient tissue imaging by desorption electrospray ionization mass spectrometry) can be performed while morphology of the tissue section is kept intact or unmodified, allowing subsequent analysis of the tissue by histochemistry or many other techniques to be performed. This is a new methodology for non-destructive, morphologically friendly tissue analysis by mass spectrometry techniques, such as desorption electrospray ionization mass spectrometry. Thus in certain aspects, the invention provides methods for analyzing tissue that involve analyzing a tissue sample using a mass spectrometry technique, in which the technique utilizes a liquid phase that does not destroy native tissue morphology during analysis. In certain embodiments, analyzing involves imaging a tissue section.

In certain embodiments, methods of the invention allow extraction of lipid species from tissue during DESI-MS analysis while morphology of the tissue remains undisturbed, therefore allowing subsequent analysis to be performed on the same tissue section. Particularly, methods of the invention allow high-quality 2D DESI-MS ion images to be directly compared and even overlaid with the H&E stained tissue section, allowing a better correlation between the spatial distribution of the lipid species detected and the substructures of a subject's brain. Pathological evaluation of the tissue sections confirmed that no morphological damage was caused to the tissue as a result of DESI-MS imaging when using appropriate solvents.

Importantly, methods of the invention allow for DESI-MS imaging of any type of sample that includes lipids, for example, human or animal tissue, plant tissue, soil, industrial chemical mixtures, and cleaning materials. In certain embodiments, the sample is human tissue. The human tissue may be epithelium tissue, healthy or diseased, such as cancerous bladder, kidney and prostate tissue. In these embodiments, DESI-MS imaging may be performed on the tissue to obtain a molecular diagnosis and then the same tissue section can be used not only for H&E staining, but also for immunohistochemistry. These advancements allow DESI-MS imaging to be included in the tissue analysis clinical workflow. They also allow more detailed diagnostic information to be obtained by combining two orthogonal techniques, imaging MS and histological examination.

In other aspects, the invention provides methods for imaging a lipid containing sample (e.g., a tissue sample) that involve imaging a lipid containing sample using a direct ambient ionization/sampling technique, in which the technique is performed in a manner that allows the sample to be subjected to further analysis after imaging.

Another aspect of the invention provides analysis methods that involve obtaining a lipid containing sample, imaging the sample using a mass spectrometry technique, in which the technique utilizes a liquid phase that does not destroy native tissue morphology during analysis, and performing a histochemistry analysis technique on the sample.

Another aspect of the invention provides methods for diagnosing cancer that involve obtaining a lipid containing sample, imaging the sample using a mass spectrometry technique, in which the technique utilizes a liquid phase that does not destroy native tissue morphology during analysis, performing a histochemistry analysis technique on the sample, and diagnosing a cancer based results of the imaging and the performing steps.

Any mass spectrometry technique known in the art may be used with methods of the invention. Exemplary mass spectrometry techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein its entirety.

Exemplary mass spectrometry techniques that utilize direct ambient ionization/sampling methods including desorption electrospray ionization (DESI; Takats et al., Science, 306:471-473, 2004 and U.S. Pat. No. 7,335,897); direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desoption/ionization (ELDI; Shiea et al., J. Rapid Communications in Mass Spectrometry, 19:3701-3704, 2005). The content of each of these references in incorporated by reference herein its entirety.

In certain embodiments, the mass spectrometry technique is desorption electrospray ionization (DESI). DESI is an ambient ionization method that allows the direct ionization of species from thin tissue sections (Takats et al., Science, 306:471-473, 2004 and Takats, U.S. Pat. No. 7,335,897). DESI-MS imaging has been successfully used to diagnose multiple types of human cancers based on their lipid profiles detected directly from tissue (Eberlin L S, Ferreira C R, Dill A L, Ifa D R, & Cooks R G (2011) Desorption Electrospray Ionization Mass Spectrometry for Lipid Characterization and Biological Tissue Imaging. Biochimica Et Biophysica Acta-Molecular And Cell Biology Of Lipids accepted).

Human bladder cancer and adjacent normal tissues were successfully distinguished on the basis of multiple marker lipids (Cooks R G, et al. (2011), Faraday Discussions 149:247-267). Multivariate statistical analysis of the DESI-MS imaging data by means of principal component analysis and partial least squares discriminant analysis allowed a successful correlation between DESI-MS data and pathological evaluation in 88% of the cases analyzed (Dill A L, et al. (2011), Chemistry—a European Journal 17(10):2897-2902). DESI-MS imaging was also applied for the diagnosis of human cancers including; two types of kidney cancer (Dill A L, et al. (2010), Analytical and Bioanalytical Chemistry 398(7-8):2969-2978); human prostate cancer (Eberlin L S, et al. (2010), Analytical Chemistry 82(9):3430-3434); and the grading of brain gliomas (WHO grade II, grade III and grade IV (glioblastoma; Eberlin L S, et al. (2010), Angewandte Chemie-International Edition 49(34):5953-5956). In addition to cancer diagnostics, DESI-MS imaging has been used to characterize tissues of other disease states, such as chemically profiling and imaging of human arterial plaques with atherosclerosis (Manicke N E, et al. (2009), Analytical Chemistry 81(21):8702-8707). In addition to the possibility of supplementing the DESI-MS solvent with ionization facilitator compounds (Jackson A U, Shum T, Sokol E, Dill A, & Cooks R G (2011), Analytical and Bioanalytical Chemistry 399(1):367-376), a unique capability of DESI-MS is the possibility to use reactants in the solvent to facilitate the ionization (reactive DESI) and detect important metabolic intermediates that can be difficult to ionize, such as cholesterol (Wu C P, Ifa D R, Manicke N E, & Cooks R G (2009), Analytical Chemistry 81(18):7618-7624).

Operated in an imaging mode, it uses a standard microprobe imaging procedure, which in this case involves moving the probe spray continuously across the surface while recording mass spectra. See for example, Wiseman et al. Nat. Protoc., 3:517, 2008, the content of which is incorporated by reference herein its entirety. Each pixel yields a mass spectrum, which can then be compiled to create an image showing the spatial distribution of a particular compound or compounds. Such an image allows one to visualize the differences in the distribution of particular compounds over the lipid containing sample (e.g., a tissue section). If independent information on biological properties of the sample are available, then the MS spatial distribution can provide chemical correlations with biological function or morphology. More over, the combination of the information from mass spectrometry and histochemical imaging can be used to improve the quality of diagnosis.

In particular embodiments, the DESI ion source is a source configured as described in Ifa et al. (Int. J. Mass Spec/rom. 259(8), 2007). A software program allows the conversion of the XCalibur 2.0 mass spectra files (.raw) into a format compatible with the Biomap software (freeware, http://www.maldo-msi.org). Spatially accurate images are assembled using the Biomap software.

Methods of the invention involve using a liquid phase that does not destroy native tissue morphology. Any liquid phase that does not destroy native tissue morphology and is compatible with mass spectrometry may be used with methods of the invention. Exemplary liquid phases include DMF, ACN, and THF. In certain embodiments, the liquid phase is DMF. In certain embodiments, the DMF is used in combination with another component, such as EtOH, $H_2O$, ACN, and a combination thereof. Other exemplary liquid phases that do not destroy native tissue morphology include ACN: EtOH, MeOH:$CHCl_3$, and ACN:$CHCl_3$.

In certain embodiments, methods of the invention involve performing a histochemical analysis on the tissue sample after it has been subjected to mass spectrometric analysis. Any histochemical analytical technique known in the art may be performed on the tissue, and the performed technique will depend on the goal of the analysis. Exemplary histochemical analytical techniques include H&E staining or immunohistochemistry.

BRIEF DESCRIPTION OF THE DRAWINGS

(FIG. 3B) m/z 888.6, ST(24:1); (FIG. 3C) m/z 890.7, ST(24:0); (FIG. 3D) m/z 885.6, PI(18:0/20:4) and (FIG. 3E) m/z 303.3, FA(20:4). Optical image of the same tissue section first imaged by DESI-MS and then H&E stained is shown in (FIG. 3F). High quality two-dimensional ion images were obtained under standard optimized DESI-MS imaging conditions at a lateral resolution of approximately 180 μm.

(FIG. 4B) m/z 885.6, PI (18:0/20:4); (FIG. 4C) m/z 835.6, PI(16:0/18:1); (FIG. 4D) m/z 281.6, FA (18:1) and (FIG. 4E) m/z 537.2 (FA dimer). After the DESI-MS imaging experiment, the same tissue sections were subjected to H&E staining (FIG. 4F), evaluated by expert pathologist, and diagnosed as cancerous and normal. Representative mass spectra of (FIG. 4G) normal and (FIG. 4H) cancerous tissue are shown. Overlay of the ion image m/z 537.2 and H&E stain of the same tissue section allowed a region of normal tissue to be detected within the cancerous tissue section (FIG. 4I).

FIGS. 5A-C. Non-destructive DESI-MS imaging allows immunohistochemistry to be performed after imaging on the same tissue section when using morphologically friendly solvent systems. Optical images of the entire tissue and magnified brightfield optical images of H&E stained and p63 IHC prostate tissue sections used are shown for (FIG. 5A) control samples, (FIG. 5B) samples imaged by DESI-MS using DMF:EtOH (1:1) as solvent system and (FIG. 5C) samples imaged by DESI-MS using standard ACN:$H_2O$ (1:1) as solvent system.

DETAILED DESCRIPTION

Figure 1A:
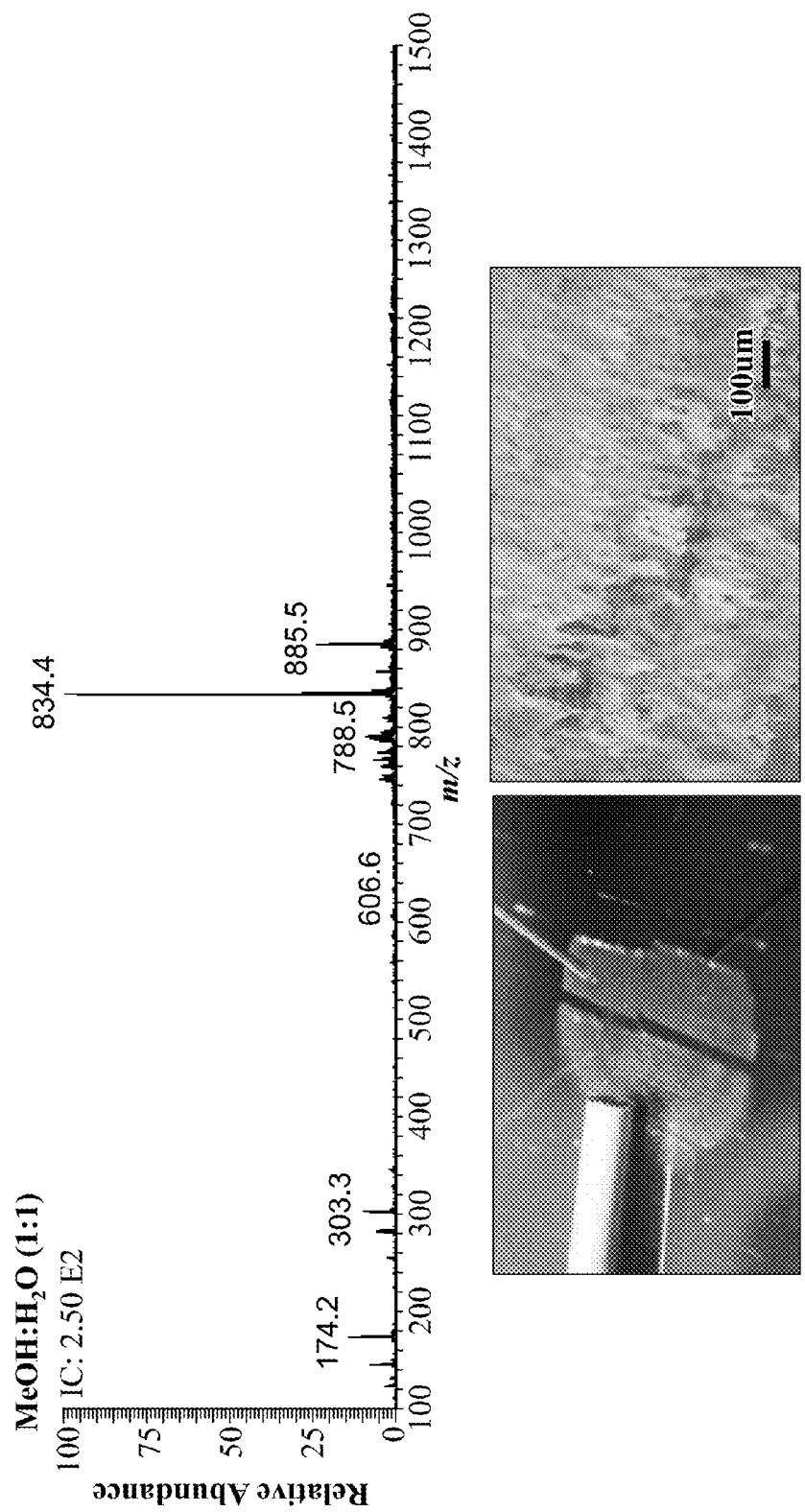
FIGS. 1A-C. Chemical information and physical effect of (FIG. 1A) standard DESI-MS solvent system MEOH:$H_2O$ (1:1) and new solvent systems (FIG. 1B) DMF:EtOH (1:1) and (FIG. 1C) DMF:$H_2O$ (1:1) on sequential 15 μm thick mouse brain tissue sections. DESI-MS mass spectra of similar regions of the gray brain matter obtained with (FIG. 1A) MEOH:$H_2O$ (1:1) and (FIG. 1B) DMF:EtOH (1:1) solvent systems show similar molecular information, while (FIG. 1C) DMF:$H_2O$ (1:1) favored the ionization of smaller m/z molecules such as fatty acids and metabolites. Insets (LHS) show an optical image of the DESI-MS imaging experiment on mouse brain tissue. The physical damage to the tissue is strikingly different between the standard solvent systems and the new morphologically friendly solvent systems. Insets (RHS) show magnified bright-field optical images of the same region of the different mouse brain tissue sections which were first imaged by DESI-MS with the different solvent systems and subsequently H&E stained.

The present invention provides new methodologies that allow mass spectrometry analysis of a lipid containing sample (e.g., DESI-MS imaging) to be performed in a non-destructive matter, so that other analyses of the same sample can be performed after the mass spectrometry analysis is performed. A particular embodiment of the invention relates to mass spectral tissue imaging using DESI. DESI-MS imaging has been increasingly applied in the biomedical field. Methods of the invention, which use a variety of solvent systems for imaging, allows DESI-MS imaging of chemical compounds to be performed on lipid containing samples (e.g., tissue sections), while the morphology of the tissue remains unmodified. After DESI-MS imaging, the tissue can be used for H&E staining, immunohistochemistry, and any other tissue analysis technique to obtain more information on the distribution of its chemical constituents.

A frozen mouse brain from a male mouse was purchased from Rockland Immunochemicals, Inc. (Gilbertsville, Pa., USA) and stored at −80° C. until it was sliced into coronary sections of varying thickness (2 μm, 3 μm, 5 μm and 15 μm) using a Shandon S M E Cryotome cryostat (GMI, Inc., Ramsey, Minn., USA) and thaw mounted onto glass slides. The glass slides were stored in a closed container at −80° C. until analysis, when they were allowed to come to room temperature and dried in a dessicator for approximately 15 minutes. All human tissue samples were handled in accordance with approved institutional review board (IRB) protocols at Indiana University School of Medicine. Six human bladder cancer and paired normal samples, four human prostate cancer and paired normal samples and one human kidney cancer and paired normal sample were obtained from the Indiana University Medical School Tissue Bank. All tissue samples were flash frozen in liquid nitrogen at the time of collection and subsequently stored at −80° C. until sliced into 5 or 10 μm thick sections. The 5 and 15 μm thick sections were used for DESI-MS imaging experiments followed by either p63 immunohistochemistry or H&E stain, respectively. Tissue sections not analyzed by DESI-MS were used in control experiments. The thin tissue sections were thaw mounted to glass slides; each slide containing one section of tumor tissue and one section of adjacent normal tissue from the same patient. The glass slides were stored in closed containers at −80° C. Prior to analysis, they were allowed to come to room temperature and then dried in a dessicator for approximately 15 minutes.

The DESI ion source was a lab-built prototype, similar to a commercial source from Prosolia Inc. (Indianapolis, Ind. USA), configured as described elsewhere (Watrous J D, Alexandrov T, & Dorrestein P C (2011), Journal of Mass Spectrometry 46(2):209-222). It consists of an inner capillary (fused silica, 50 µm i.d., 150 µm o.d.) (Polymicro Technologies, AZ, USA) for delivering the spray solvent and an outer capillary (250 µm i.d., 350 µm o.d.) for delivering nitrogen nebulizing gas. The DESI spray was positioned 2.5 mm from the tissue sample at an incident angle of 54°. A low collection angle of 10° was chosen to ensure the most efficient collection of the material being desorbed. The distance between the spray and the inlet was 6.0 mm. Multiple spray solvent systems were tested in the experiments, including ACN, $H_2O$, MeOH, ethanol (EtOH), tetrahydrofuran (THF), N,N-dimethylformamide (DMF), chloroform ($CHCl_3$), acetone and many of their binary mixtures in a ratio of (1:1). The only tertiary mixture investigated was of $ACN:H_2O:DMF$ at different v/v proportions, such as (8:3:1 and 1:1:1). DESI-MS experiments were carried out in the negative ion mode, using a 5 kV spray voltage and a flow rate of 0.5-1.5 µL/min depending on the solvent system of choice. The nebulizing gas (N2) pressure was set for all experiments at 175-180 psi. The mass spectrometer used was a LTQ linear ion trap mass spectrometer controlled by XCalibur 2.0 software (Thermo Fisher Scientific, San Jose, Calif., USA).

Analysis were performed using an imaging approach. The tissues were scanned using a 2D moving stage in horizontal rows separated by a 150 µm vertical step for the mouse brain imaging assay (FIG. 3), and 250 µm vertical step for the human tissue imaging assays. For the DESI-MS assay shown in FIG. 2, the same mouse brain section was imaged 10 times with DMF:EtOH (1:1) and each analysis was performed in 10 lines of 250 µm. After one analysis was concluded, the moving stage was set to coordinate 0,0 (x,y) for the new analysis to be performed. The surface moving stage included an XYZ integrated linear stage (Newport, Richmond, Calif., USA) and a rotary stage (Parker Automation, Irwin, Pa., USA). A software program allowed the conversion of the XCalibur 2.0 mass spectra files (.raw) into a format compatible with the Biomap software (freeware, http://www.maldi-msi.org). Spatially accurate images were assembled using the BioMap software. The color scale is normalized to the most intense (100% relative intensity) peak in the mass spectra.

Tissue sections were subjected to H&E staining after DESI-MS imaging analysis or after being dried in a dessicator (control sections). All chemicals used for the H&E staining were purchased from Sigma-Alrich (St. Louis, Mo., USA). The H&E staining was performed at room temperature: dip in MeOH for 2 minutes, rinse in water (10 dips), stain in Harris modified hematoxylin solution for 1.5 minutes, rinse in water (10 dips), 1 quick dip in 0.1% ammonia (blueing agent), rinse in water (10 dips), counterstain in Eosin Y (8 seconds), rinse in 100% EtOH (10 dips), rinse again in 100% EtOH (10 dips), rinse in Xylene (6 dips) and rinse again in Xylene (6 dips). Sections were allowed to dry and covered with a glass cover slide. Immunohistochemistry assays were performed in the Veterinary Department at Purdue University by Dr. Carol Bain, in accordance to their standard protocol. The primary antibody p63 (4A4):sc-8431 was purchased from Santa Cruz Biotechnology, INC (Santa Cruz, Calif., USA).

Pathological evaluation of the human tissue sections that were either H&E stained or subjected to p63 immunohistochemistry was performed by Dr. Liang Cheng, at IU School of Medicine in a blind fashion. Optical images of tissue sections were obtained using a SM-LUX Binocular Brightfield Microscope (Leitz, Wetzlar, Germany) under 16, 25 and 40× magnification.

The solvent system used in DESI tissue imaging is taught to be an important technical parameter for optimization (Badu-Tawiah A, Bland C, Campbell D I, & Cooks R G (2010), Journal of the American Society for Mass Spectrometry 21(4):572-579; and Green F M, Salter T L, Gilmore I S, Stokes P, & O'Connor G (2010), Analyst 135(4):731-737). Many studies have shown that the chemical and physical properties of the solvent system used affect the molecular information obtained during DESI-MS tissue imaging (Ellis S R, et al. (2010), J. Am. Soc. Mass Spectrom. 21(12):2095-2104). Optimization of the spray composition allows targeted classes of compounds to be enhanced depending on the overall goal. Besides the chemical information, the effect of the solvent system on the morphology of the tissue being analyzed is a factor in DESI-MS imaging. Commonly used DESI-MS imaging solvent systems, such as mixtures of water with methanol or acetonitrile (Wiseman J M, Ifa D R, Venter A, & Cooks R G (2008), Nature Protocols 3(3):517-524), with or without an acidic modifier, yield extensive chemical information but are known to cause depletion and destruction of the tissue sections, precluding any consecutive analysis to be performed. To overcome these problems, different solvents such as ACN, $H_2O$, MeOH, ethanol (EtOH), tetrahydrofuran (THF), N,N-dimethylformamide (DMF), chloroform ($CHCl_3$), acetone and mixtures of these were investigated in the analysis of 15 µm thick serial coronary mouse brain tissue sections.

A binary mixture of $MEOH:H_2O$ (1:1, v/v) or $ACN:H_2O$ (1:1, v/v) has been commonly used in DESI imaging of brain tissue, yielding high signal intensity for polar lipids and free fatty acids (Eberlin L S, Ifa D R, Wu C, & Cooks R G (2010), Angewandte Chemie-International Edition 49(5): 873-876; and Wiseman J M, Ifa D R, Song Q Y, & Cooks R G (2006), Angewandte Chemie-International Edition 45(43):7188-7192). The majority of the ions observed in the mass spectra obtained from the solvent systems tested here correspond to commonly observed lipid species in brain tissue when using standard $MeOH:H_2O$ (1:1), such as deprotonated free fatty acids, phosphatidylserines (PS), phosphatidylinositols (PI) and sulfatides (ST) (Eberlin L S, Ifa D R, Wu C, & Cooks R G (2010), Angewandte Chemie-International Edition 49(5):873-876). Variations in the relative abundance of the lipid species and in the total ion signal obtained were observed depending on the solvent composition. For instance, spectra obtained when using pure methanol as the solvent system showed higher relative abundance of fatty acid dimers in the m/z 500-700 region of the mass spectrum. In particular, it was observed that pure DMF yielded spectra with high total abundance and with chemical information which is very similar to that which is obtained using $MeOH:H_2O$.

Interestingly, the DMF spray was observed to not cause tissue destruction. The effect of DMF in the tissue was further explored by combining this solvent with other solvents in binary (1:1 v/v) and tertiary mixtures. The combination of DMF with either ACN, EtOH, THF or $CHCl_3$ yielded very high ion signal and chemical information similar to what is seen using $MeOH:H_2O$. Combinations of DMF with either $H_2O$ or MeOH greatly enhanced the signal of low molecular weight compounds, such as small metabolites, FAs and FA dimers (Eberlin L S, Ferreira C R, Dill A L, Ifa D R, & Cooks R G (2011) Desorption Electrospray Ionization Mass Spectrometry for Lipid Characterization and Biological Tissue Imaging. Biochimica Et Biophysica Acta-Molecular And Cell Biology Of Lipids accepted). In terms of spray stability and total ion abundance, the combinations of DMF with either EtOH or ACN are great solvent systems for tissue imaging experiments. The change in chemical information obtained by DESI-MS using different solvent combinations can be compared to the use of different matrices in MALDI imaging, but in DESI-MS imaging experiments, the "matrix" is delivered in real-time, spot-by-spot, without the need for sample preparation or without causing spatial delocalization of molecules.

Figure 1B:
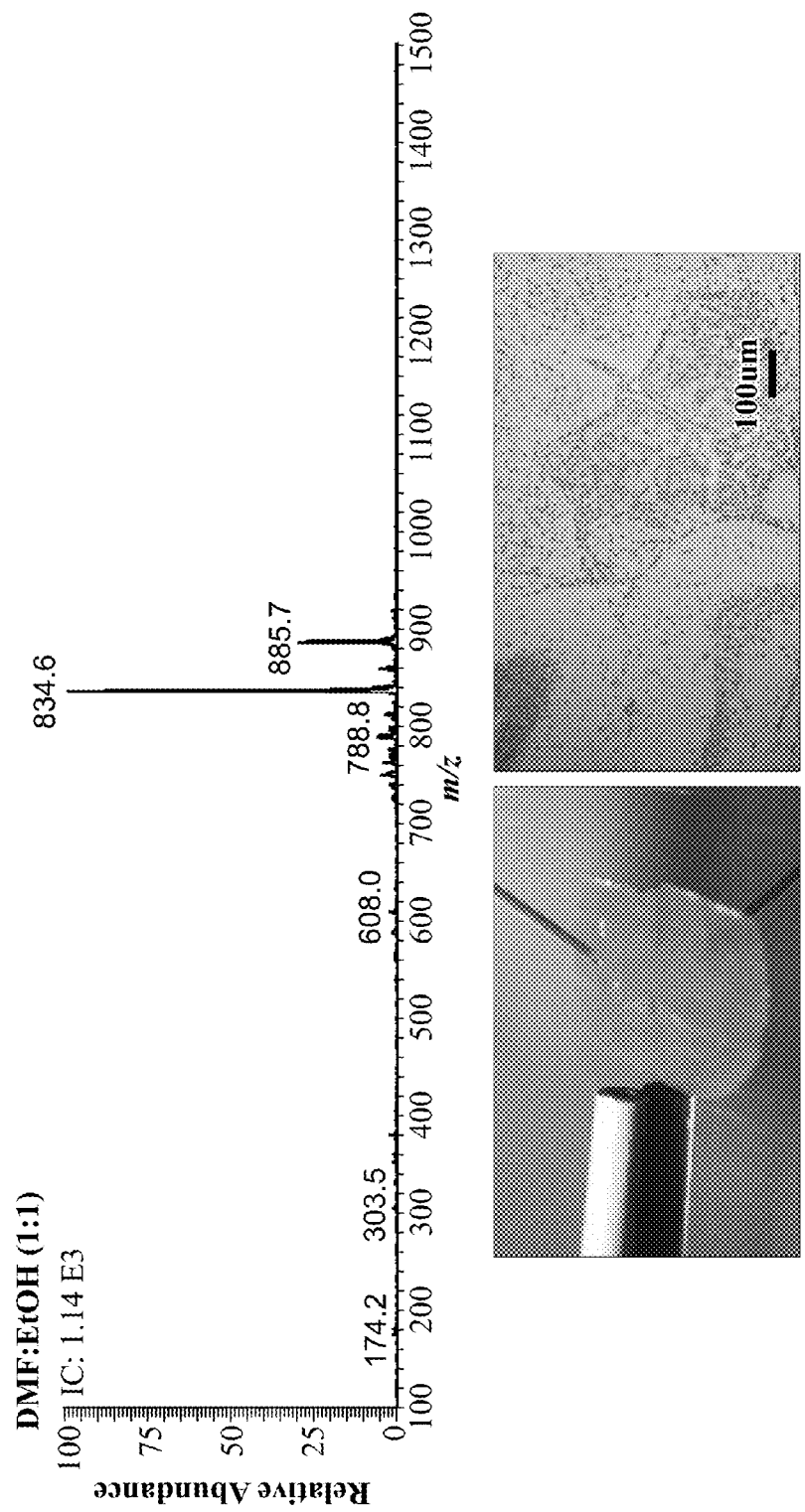
Figure 1C:
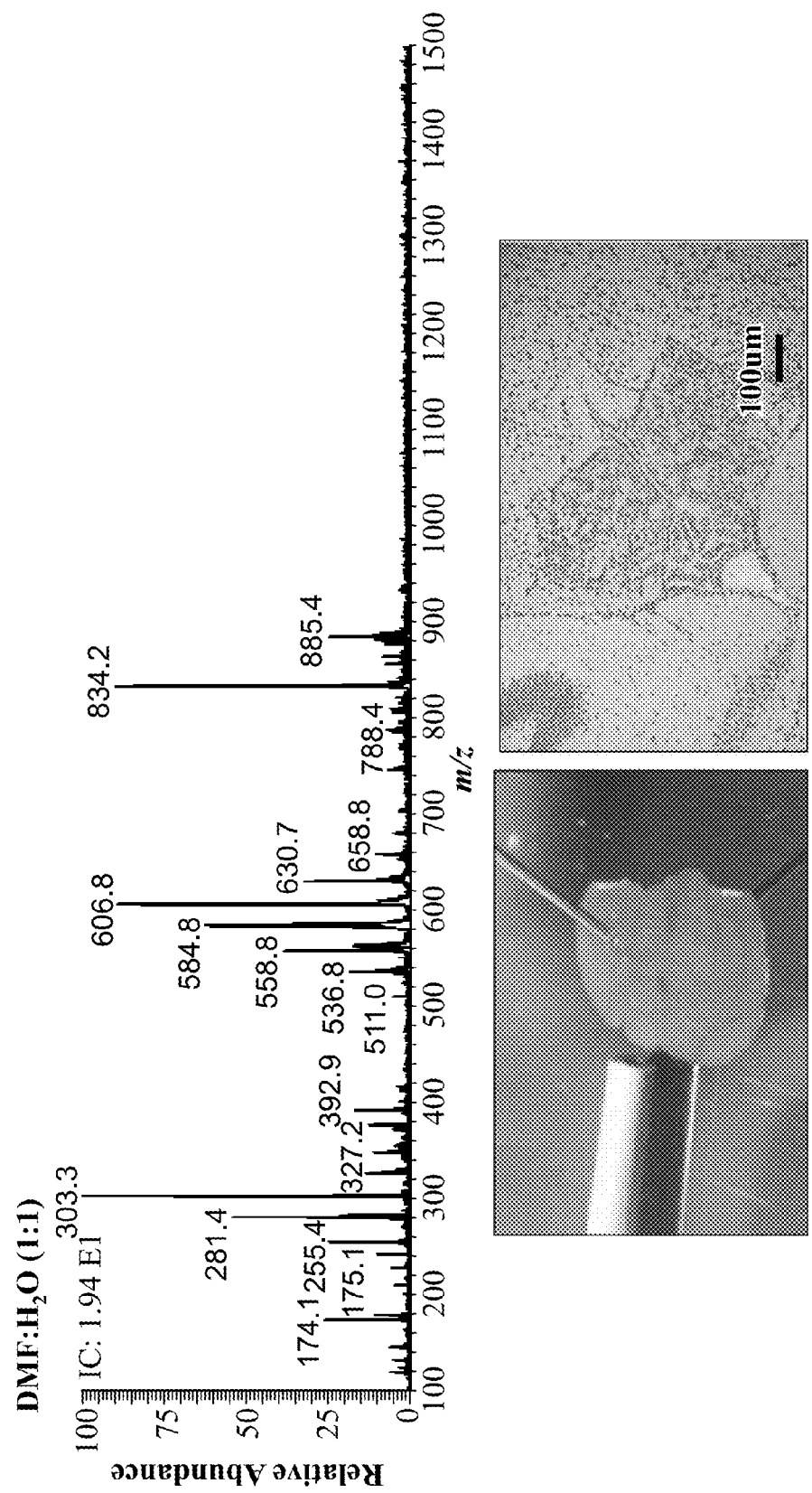

Importantly, none of these solvent combinations were observed to cause visual damage to the 15 µm thick tissue sections that were analyzed. FIG. 1 shows the physical and chemical effect of two of the new solvent systems developed, DMF:EtOH (1:1) and DMF:$H_2O$ (1:1) in comparison to the standard MEOH:$H_2O$ solvent system. DESI-MS conditions were kept identical in all analyses performed. It is striking to observe that while extensive chemical information was obtained from the tissue sections when using DMF:$H_2O$ and DMF:EtOH, tissue integrity was preserved.

As observed in the optical images shown of the DESI-MS experiment, damage to the tissue was insignificant when using DMF solvent systems. To confirm preservation of tissue integrity, H&E staining was performed on the tissue sections previously analyzed by DESI-MS. H&E staining is a commonly used histochemical protocol to evaluate cellular structure and tissue morphology by light microscopy. Careful microscopic examination of the H&E tissue sections revealed no damage or change in the cellular morphology of the sample after DESI analysis using DMF:EtOH and DMF:$H_2O$ solvent systems, while the tissue analyzed using MeOH:$H_2O$ was found to be altered and damaged, as was macroscopically observed. DESI-MS analysis of sequential mouse brain tissue sections of 2, 3 and 5 µm thicknesses was also performed, and sequential H&E staining of the tissue sections also revealed that no morphological damage occurred following DESI-MS analysis using DMF:EtOH or DMF:ACN as the solvent system.

Figure 2A:
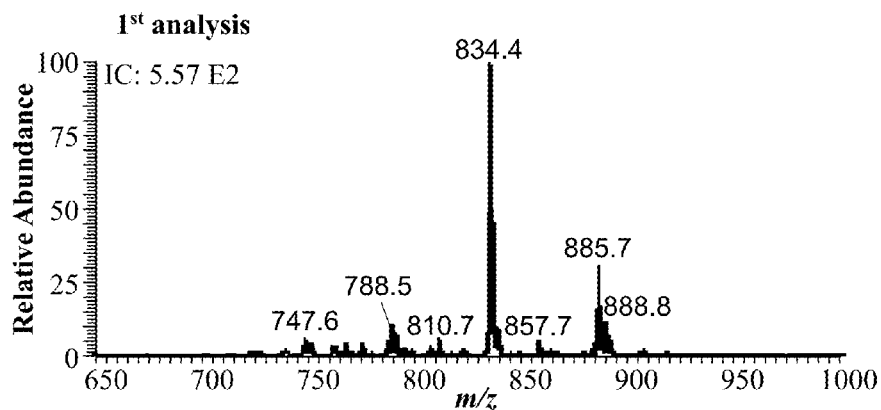
FIGS. 2A-B. Repeated DESI-MS imaging analysis of a mouse brain tissue section using DMF:EtOH as the solvent system. Mass spectra of gray matter region of a 15 μm thick mouse brain tissue section is shown for the (FIG. 2A) $1^{st}$ and (FIG. 2B) $10^{th}$ DESI-MS analysis of the same tissue section.
Figure 2B:
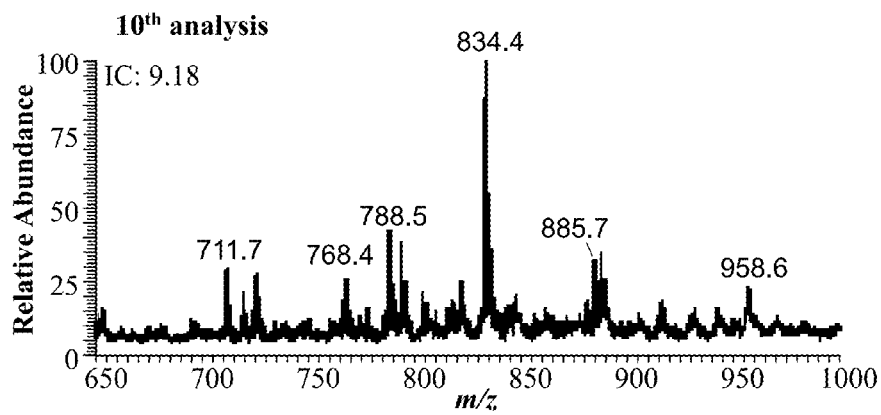
Figure 2C:
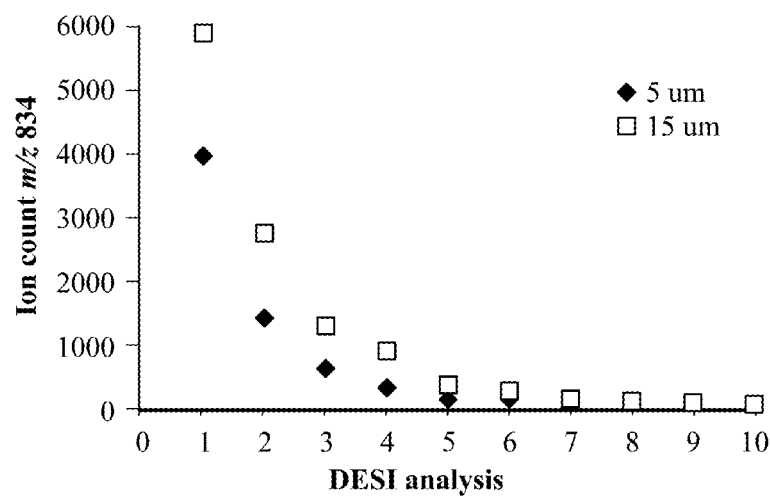
FIG. 2C shows a plot of the total intensity of the major ion m/z 834.4 (PS 18:0/22:6) obtained for the 15 μm thick mouse brain tissue and for a 5 μm thick mouse brain tissue section which was subjected to the same repeated imaging experiment. The decay profile of the ion signal with DESI analysis repetition is consistent with the accepted extraction mechanism.
Figure 3A:
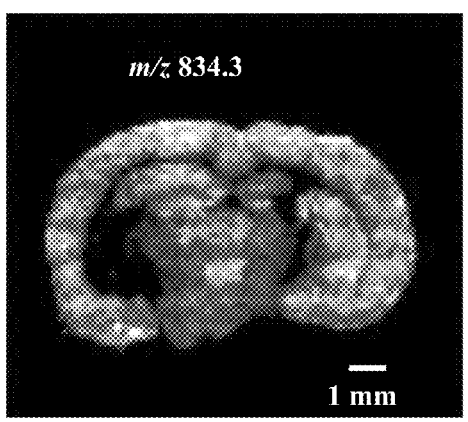
FIGS. 3A-E. DESI-MS ion images obtained from a 15 μm thick mouse brain coronal section using DMF:EtOH (1:1) as the solvent system showing the distribution of the ions at (FIG. 3A) m/z 834.3, PS(18:0/22:6)
Figure 3B:
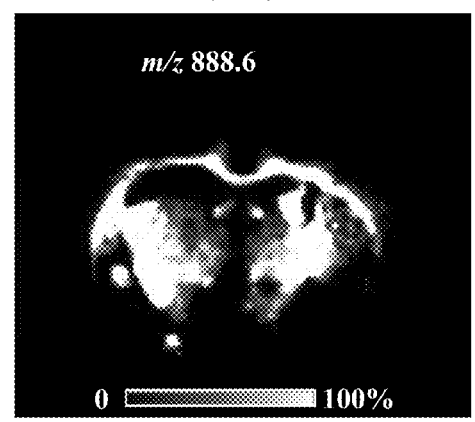
Figure 3C:
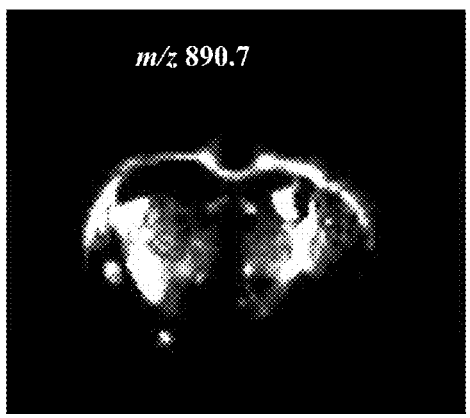
Figure 3D:
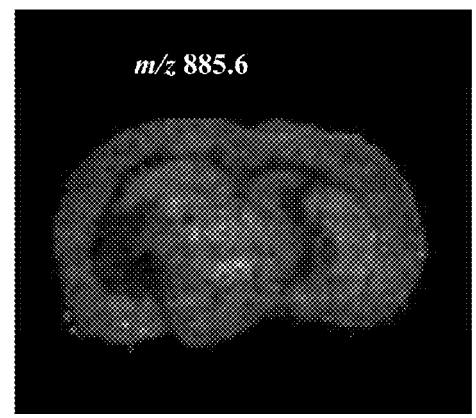
Figure 3E:
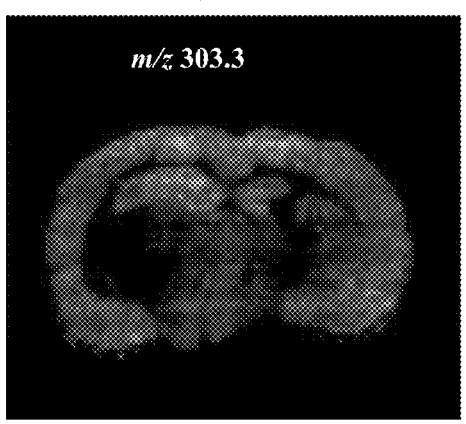
Figure 3F:
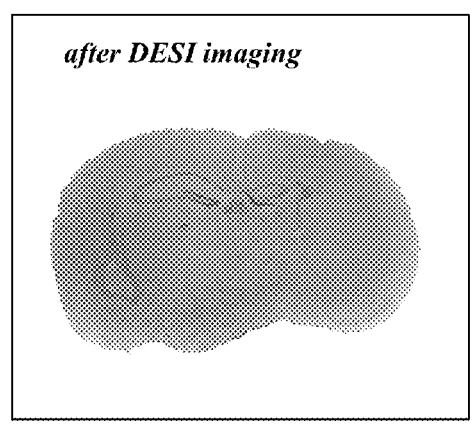

The physical and chemical effect of the DMF:EtOH solvent system was further investigated by performing several DESI-MS analyses of the same mouse brain tissue section. The same tissue region of a 5 µm and a 15 µm thick tissue section were analyzed 10 times using the DESI-MS moving stage system. Mass spectra were recorded for 10 rows (250 µm step size) of each mouse brain section and after 10 analyses had been performed, each tissue section was H&E stained and observed under brightfield microscopy under 16-40× magnification. FIGS. 2A and B show the mass spectra obtained from the gray matter region of the 5 µm thick mouse brain tissue section from the $5^{th}$ row scanned using DMF:EtOH in the $1^{st}$ and $10^{th}$ DESI-MS analysis, respectively. The ion count is approximately 60 times greater in the $1^{st}$ analysis of the mouse brain compared to the ion count obtained in the $10^{th}$ analysis of the same region. The ion count of the main ion observed in the gray matter region of the $5^{th}$ row scanned, m/z 834.4 (PS 18:0/22:6), was plotted as a function of the DESI-MS analysis number for both the 5 µm and a 15 µm thick tissue sections, shown in FIG. 2C.

Interestingly, the signal of the typical ion of m/z 834.4 obtained in the $3^{rd}$ or even $4^{th}$ DESI-MS analysis is still observed at high intensities. Furthermore, the decay profile of the ion count is consistent with the extraction mechanism proposed for DESI-MS (Costa A B & Cooks R G (2008), Chem. Phys. Lett. 464(1-3):1-8). While a MeOH:$H_2O$ spray extracts the chemical compounds from the tissue cells resulting in tissue damage, the DMF based solvent system is able to extract the chemical compounds from the tissue section without disturbing the tissue morphology. H&E staining of both a 5 µm and a 15 µm thick tissue section after ten DESI-MS imaging analyses revealed no damage to the tissue, indicating that the repetitive removal of the phospholipids by the DESI solvent spray does not affect the morphology of the cells. In fact, the extraction process that occurs in DESI-MS is comparable to the fixative procedures commonly used in histology for lipid removal (DiDonato D & Brasaemle D L (2003), Journal of Histochemistry & Cytochemistry 51(6):773-780), such as the alcohol wash used in the initial step of the H&E staining data. This alcohol wash step extracts the majority of cellular phospholipids while the cellular cytoskeletal elements are kept intact. Since hematoxylin stains nucleoproteins and eosin stains intracellular and extracellular proteins, the removal of the lipid content with conservation of the tissue integrity by DESI-MS should not interfere with this standard histochemistry protocol. Importantly, the use of DMF based solvent systems or even other solvent systems with similar morphologically-friendly properties allows pathological evaluation to be performed on the same tissue section previously analyzed by DESI-MS but with acquisition of complementary results.

All combinations of DMF with other solvents used in the DESI-MS assays on mouse brain tissue sections were found to not destroy the native morphology of the tissue. Other pure solvents, such as ACN, DMF, THF, ethanol and others did not cause damage to the tissue integrity as observed in the H&E stains. A few other combinations that did not contain DMF, such as ACN:EtOH (1:1), MeOH:$CHCl_3$ (1:1) and ACN:$CHCl_3$ (1:1), did not destroy the native morphology of the tissue. The morphological effect that the DESI spray has on tissue appear to be related to the physical and chemical properties of the solvent systems itself.

While solubility of the proteic cellular and extracellular components of the tissue section in the DESI spray solvent system plays a role in the conservation of the tissue morphology integrity, the physical properties of the solvent system such as surface tension and its effects on the dynamics of the DESI spray primary droplets also impact the damage caused to the tissue. When solubilization of cellular and extracellular components that keep cellular morphological integrity intact occurs, the tissue becomes more susceptible to the mechanical action of the DESI spray droplets. Therefore, tissue damage should be related to both solubilization of tissue components and mechanical action of the DESI spray system. The fact that the morphologically-friendly solvent systems described here do not disturb tissue integrity appear to be related to the physical properties of the DESI spray primary droplets, but also on the solubility of tissue components on the solvent system.

Chemical information and image quality are important factors in DESI-MS imaging applications. The geometric parameters of the DESI spray as well as the choice of solvent system, gas pressure and solvent flow are important when optimizing imaging conditions. When the solvent system is modified, it is important to observe that the spray spot is stable and that the ion signal intensity is maximized for obtaining good quality 2D chemical images.

FIG. 3 shows ion images of a mouse brain tissue section obtained using DMF:EtOH as the solvent system. The spray geometry and gas pressure conditions used in this imaging experiment are standard for DESI-MS imaging applications (Eberlin L S, Ifa D R, Wu C, & Cooks R G (2010), Angewandte Chemie-International Edition 49(5):873-876; and Ifa D R, Wiseman J M, Song Q Y, & Cooks R G (2007), International Journal of Mass Spectrometry 259(1-3):8-15). In terms of solvent flow, it was observed that at a regular DESI-MS imaging flow rate of 1.5 μL/min a larger spot size is obtained with DMF solvent combinations as compared to standard mixtures of water with MEOH or ACN at the same flow. The high stability and larger diameter of the spray spot can be associated with the higher boiling point of DMF (153° C.), when compared to the boiling point of solvents as MeOH and ACN. Smaller diameter spray spots can be achieved by using either a lower solvent flow rate or by mixing DMF with a higher ratio of a solvent with higher volatility, such as a mixture of DMF:EtOH (1:2). A solvent flow of 0.5 μL/min was used for the mouse brain imaging experiments using binary mixtures of DMF so that a spot size of approximately 180 μm was obtained. Lower solvent consumption as a result of using a lower flow rate is advantageous in DESI-MS imaging applications.

In the images shown in FIG. 3, two distinctive MS peak patterns associated with the lipid compositions representative of the gray and white matter of the brain were observed in the negative-ion mode for the brain section analyzed (Eberlin L S, Ifa D R, Wu C, & Cooks R G (2010), Angewandte Chemie-International Edition 49(5):873-876). The ion images of m/z 834.3, PS 18:0/22:6 (FIG. 3A), m/z 885.6, PI 18:0/20:4 (FIG. 3D) and m/z 303.3,FA 20:4 (FIG. 3E) show a homogeneous distribution in the brain gray matter, which are complementary and distinct from the ion images of m/z 888.8 (ST 24:1, FIG. 3B) and m/z 890.7 (ST 24:0, FIG. 3C), which are homogeneously distributed in the mouse brain white matter. FIG. 3F shows the optical image of the same tissue section which was H&E stained after DESI-MS imaging was performed. This order of analysis in which ambient MS imaging is performed followed by histochemical analysis of the same tissue section is comparable to the "post-acquisition staining" methodology used in MALDI-MS imaging (Schwamborn K, et al. (2007), International Journal of Molecular Medicine 20(2):155-159). The high-quality 2D DESI-MS ion images can be directly compared and even overlaid with the H&E stained tissue section, allowing a better correlation between the spatial distribution of the lipid species detected and the substructures of the mouse brain.

The capability to perform DESI-MS imaging and histochemical analysis of the same tissue section is important in the investigation of diseased tissue. The comparison of histological features from stained sections with corresponding molecular images obtained by ambient imaging MS is important for accurate correlations between molecular signatures and tissue disease state. This is especially true in the analysis of cancerous tissue sections which are very often highly heterogeneous, with regions of containing various tumor cell concentrations (Agar NYR, et al. (2011), Neurosurgery 68(2):280-290), infiltrative normal tissue (Dill A L, et al. (2011), Chemistry—a European Journal 17(10): 2897-2902), precancerous lesions (Eberlin L S, et al. (2010), Analytical Chemistry 82(9):3430-3434), etc. Integration of DESI-MS imaging into a traditional histopathology workflow required that the mass spectrometric analysis not interfere with the morphology of the tissue section. Provided this is the case, the combination of the two different types of data (as represented by the case of superimposed images) greatly increases discrimination between different tissue types including that between diseased and healthy tissue.

Figure 4A:
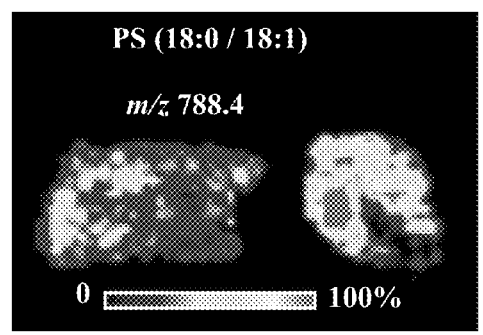
FIGS. 4A-E. DESI-MS imaging of human bladder cancerous and adjacent normal tissue sections using morphology friendly DMF:EtOH (1:1) as the solvent system. Ion images show the distribution of (FIG. 4A) m/z 788.4, PS(18:0/18:1)
Figure 4B:
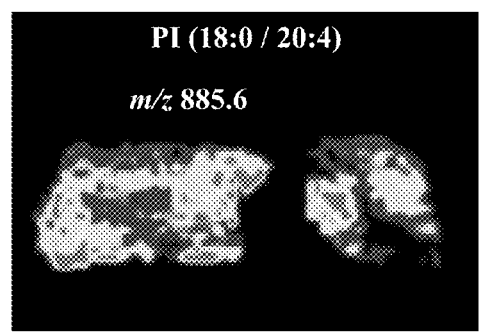

To investigate this capability, human bladder, kidney and prostate cancer tissues along with adjacent normal samples were analyzed by DESI-MS imaging in the negative ion mode using one of our histology compatible solvent system and sequentially H&E stained. The lipid species present in the tissue sections were identified based on collision-induced dissociation (CID) tandem MS experiments and comparison of the generated product ion spectra with literature data (Hsu F F & Turk J (2000), Journal of the American Society for Mass Spectrometry 11(11):986-999). FIG. 4 shows a series of negative ion mode DESI-MS ion images of species commonly observed in human bladder transitional cell carcinoma and adjacent normal tissue from sample UH0210-13. FIGS. 4A, B, C, D and E show the ion images obtained for the ions at m/z 788.4 (PS(18:0/18:1)), m/z 885.6 (PI(18:0/20:4)), m/z 835.6 (PI(16:0/18:1)), m/z 281.6 (FA 18:1) and m/z 537.2 (FA dimer).

Figure 4C:
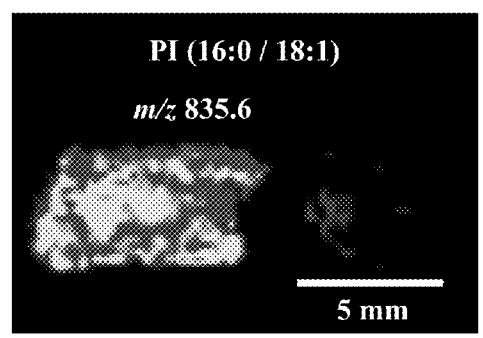
Figure 4D:
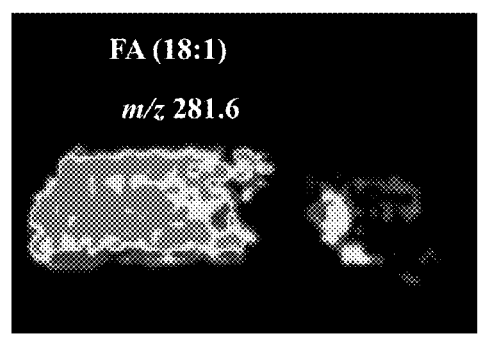
Figure 4E:
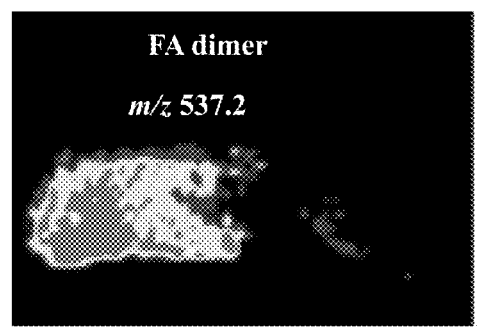

As previously reported for DESI-MS imaging of human bladder cancer in combination with statistical analysis using a standard ACN:$H_2O$ (1:1) solvent system, the ions that most significantly contribute to the discrimination between cancerous and normal bladder tissue are the free fatty acid and the fatty acid dimers, which consistently appear at increased intensities in the ion images of cancerous tissue when compared to normal tissue using the morphology friendly solvent system, DMF:EtOH (1:1) (FIGS. 4C and D; Dill A L, et al. (2011), Chemistry—a European Journal 17(10): 2897-2902; and Dill A L, et al. (2009), Analytical Chemistry 81(21):8758-8764). Representative mass spectra obtained for the cancerous and normal tissue sections are shown in FIGS. 4G and H. Many other individual ions observed in the mass spectra were found at different intensities in the normal and cancerous tissues as observed in extracted DESI-MS ion images.

Figure 4F:
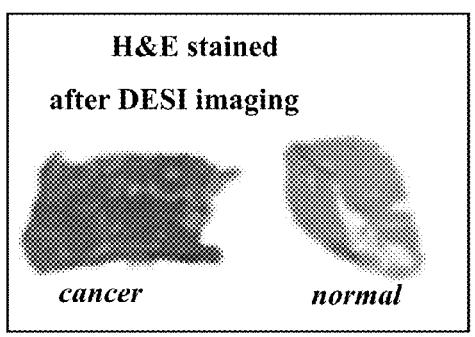
Figure 4G:
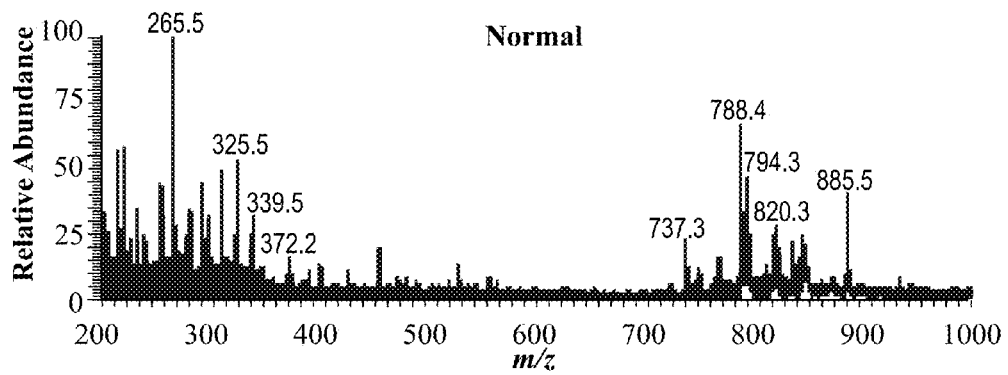
Figure 4H:
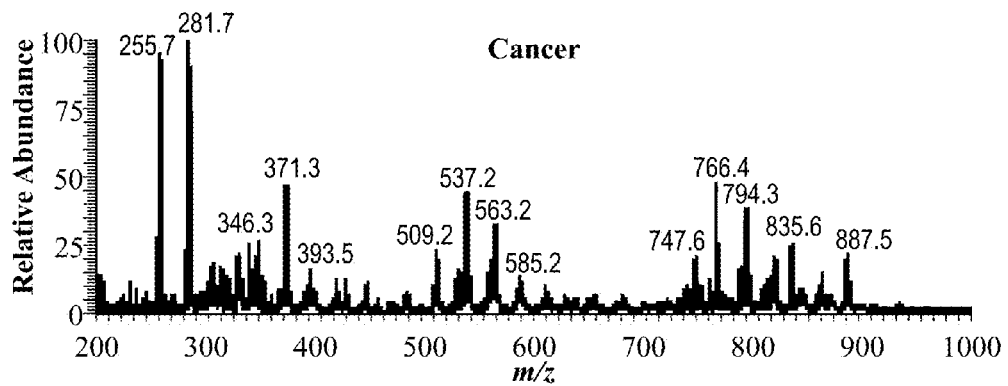
Figure 4H:
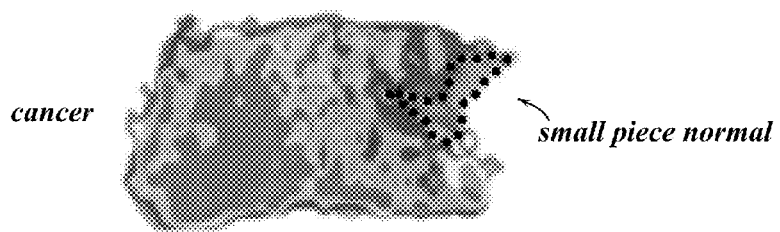

The optical image of the same tissue sections stained with H&E after DESI-MS imaging analysis is shown in FIG. 4F and were used to obtain a histopathological diagnosis. Detailed pathological examination of the H&E stained sections confirmed that there was no morphological damage to the tissue sections as a result of DESI-MS imaging analysis, allowing a straightforward diagnosis of the sections as cancerous and normal. No difference in cell morphology or tissue integrity was observed at the microscopic scale when the H&E stained tissue section of the DESI-MS imaged tissue was compared to a control tissue section.

The non-destructive nature of the DMF based solvent system enables ion images to be overlaid with the H&E stain of the same tissue section for unambiguous diagnosis and correlation. For example, a small region of tissue within the cancerous section detected by DESI-MS as negative for bladder cancer based on the distribution of the FA dimer m/z 537.2 was confirmed as normal tissue by pathological evaluation of the overlaid DESI-MS ion image and H&E stain of the same tissue section. This unambiguous correlation is made possible through the use of the morphologically friendly solvent systems so that the histological data can be considered in combination with the DESI-MS imaging data. H&E stained serial sections of the same sample imaged using standard ACN:$H_2O$ (1:1) revealed that the tissue integrity was completely destroyed and were inadequate for pathological evaluation. The same histological observation that DESI imaging is histology compatible was obtained in the analysis of the H&E stained sections of five other human bladder cancer and paired normal samples, four human prostate cancer and paired normal samples and one kidney cancer and paired normal sample initially imaged by DESI-MS with a morphologically friendly solvent system.

Previously reported molecular information that allowed a diagnosis to be obtained for these types of cancer was consistent using the new solvent system. The capability of DESI-MS imaging to be histology compatible was further investigated by performing immunohistochemical (IHC) analysis with p63 antibody on bladder and prostate cancer tissue sections, which was performed after DESI-MS imaging. The gene p63 is one of the most commonly used basal cell-specific markers in the diagnosis of prostate cancer, whose expression is known to be down-regulated in adenocarcinoma of the prostate when compared to normal prostate tissue (Signoretti S, et al. (2000), American Journal of Pathology 157(6):1769-1775). Negative IHC staining of tumor protein p63 is commonly used as a clinical tool for identifying prostate cancerous tissue. The role of p63 in bladder carcinogenesis is not as clear as in prostate cancer (Comperat E, et al. (2006), Virchows Archiv 448(3):319-324), and positive staining of p63 is typically associated with both benign and malignant bladder epithelial cells.

Two bladder cancer samples and two prostate cancer samples were subjected to p63 IHC after DESI-MS imaging on the same tissue section. Detailed pathological evaluation of the tissue sections that were subjected to IHC after DESI-MS imaging confirmed that the DESI-MS analysis of the tissue lipid content did not interfere with the p63 IHC protocol, as the tissue remained intact after the imaging experiment. p63 IHC of the bladder sample was found to be positive for both cancerous and normal tissue sections. For the prostate cancer sample, UH0002-20, it was subjected to p63 IHC after DESI-MS imaging and again no damage to the morphology of the tissue was observed (FIG. 5), allowing a diagnosis of cancerous and adjacent normal tissue to be achieved, which correlated with the cholesterol sulfate signal previously reported as a possible prostate cancer biomarker using DESI-MS imaging (Eberlin L S, et al. (2010), Analytical Chemistry 82(9):3430-3434.). Also, these findings confirmed that protein position in the tissue samples remained unchanged, which is probably due to the insolubility of these proteins in the solvent combinations used.

The results reported here introduce a novel capability of histologically compatible ambient molecular imaging by DESI-MS. The feasibility of DESI-MS imaging to be performed while tissue integrity and cell morphology is conserved allows ambient mass spectrometric analysis of tissue to be combined with traditional histopathology with the goal of providing better disease diagnostics. As DESI-MS imaging using histologically friendly solvent systems does not interfere with pathological analysis, the technique could be included as the initial step in the clinical tissue analysis workflow.

Methods reported herein will allow DESI-MS to be more broadly applied in the biomedical field, such as in intraoperative applications. In additional to biomedical applications, the morphologically compatible solvent system allows DESI-MS imaging to be combined to other analytical techniques for chemical analysis of the same tissue section.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method for analyzing a tissue sample, the method comprising:
    performing a mass spectral analysis of a tissue sample using a desorption electrospray ionization (DESI) technique that comprises directing a liquid phase that does not destroy native tissue morphology from a DESI probe onto the tissue sample to thereby desorb one or more lipids, peptides, or proteins from the sample that are analyzed by a mass spectrometer;
    producing a mass spectral image of the tissue sample based on results of the mass spectral analysis;
    performing a histochemistry analysis technique on the sample to thereby stain the sample;
    producing an optical image of the stained sample;
    overlaying the mass spectral image with the optical image of the stained sample to produce an overlaid image; and
    determining a distribution of the one or more lipids, peptides, or proteins in the tissue sample based on an analysis of the overlaid image.

2. The method of claim 1, wherein the liquid phase is a solvent comprising dimethylformamide (DMF), acetonitrile (ACN), or tetrahydrofuran (THF).

3. The method according to claim 2, wherein the liquid phase comprises at least one other component.

4. The method according to claim 3, wherein the at least one other component is selected from the group consisting of ethanol (EtOH), water ($H_2O$), acetonitrile (ACN), and a combination thereof.

5. The method according to claim 1, wherein the liquid phase is selected from the group consisting of: acetonitrile (ACN):ethanol (EtOH); methanol (MeOH):chloroform ($CHCl_3$); and acetonitrile (ACN):chloroform ($CHCl_3$).

6. The method according to claim 1, wherein the histochemistry analysis technique is H&E staining.

7. The method according to claim 1, wherein the one or more lipids are analyzed by the mass spectrometer.

8. The method according to claim 1, wherein the ionization probe is a desorption electrospray ionization probe.

9. The method according to claim 1, further comprising determining whether an abnormality exists in the tissue sample based on the distribution of the one or more lipids, peptides, or proteins in the tissue sample.

10. The method according to claim 9, wherein the abnormality is a cancer.

11. A method for detecting cancerous tissue within a tissue sample, the method comprising:
    performing a mass spectral analysis of a tissue sample using a desorption electrospray ionization (DESI) technique that comprises directing a liquid phase that does not destroy native tissue morphology from lipids, peptides, or proteins a DESI probe onto the tissue sample to thereby desorb one or more lipids, peptides, or proteins from the sample that are analyzed by a mass spectrometer;
    producing a mass spectral image of the tissue sample based on results of the mass spectral analysis;
    performing a histochemistry analysis technique on the sample to thereby stain the sample;
    producing an optical image of the stained sample;
    overlaying the mass spectral image with the optical image of the stained sample to produce an overlaid image; and
    detecting cancerous tissue within the tissue sample based on an analysis of the overlaid image.

12. The method of claim 11, wherein the liquid phase is a solvent comprising dimethylformamide (DMF), acetonitrile (ACN), or tetrahydrofuran (THF).

13. The method according to claim 12, wherein the liquid phase comprises at least one other component.

14. The method according to claim 13, wherein the at least one other component is selected from the group consisting of ethanol (EtOH), water ($H_2O$), acetonitrile (ACN), and a combination thereof.

15. The method according to claim 11, wherein the liquid phase is selected from the group consisting of: acetonitrile (ACN):ethanol (EtOH); methanol (MeOH):chloroform ($CHCl_3$); and acetonitrile (ACN):chloroform ($CHCl_3$).

16. The method according to claim 11, wherein the histochemistry analysis technique is H&E staining.

17. The method according to claim 11, wherein the one or more lipids are analyzed by the mass spectrometer.

18. The method according to claim 11, wherein the ionization probe is a desorption electrospray ionization probe.

19. The method according to claim 11, wherein the desorption electrospray ionization probe operates at atmospheric pressure and temperature.

* * * * *